(12) United States Patent
Getts et al.

(10) Patent No.: US 8,653,251 B2
(45) Date of Patent: Feb. 18, 2014

(54) METHODS AND KITS FOR NUCLEIC ACID AMPLIFICATION

(75) Inventors: Robert C. Getts, Collegeville, PA (US); James Kadushin, Gilbertsville, PA (US); Kelly Sensinger, East Greenville, PA (US)

(73) Assignee: Genisphere Inc., Hatfield, PA (US)

( * ) Notice: Subject to any disclaimer, the term of this patent is extended or adjusted under 35 U.S.C. 154(b) by 383 days.

(21) Appl. No.: 13/013,000

(22) Filed: Jan. 25, 2011

(65) Prior Publication Data

US 2011/0124083 A1   May 26, 2011

Related U.S. Application Data

(60) Division of application No. 11/714,989, filed on Mar. 6, 2007, now Pat. No. 7,888,018, which is a continuation of application No. 11/269,021, filed on Nov. 8, 2005, now abandoned.

(51) Int. Cl.
  *C07H 21/04* (2006.01)
(52) U.S. Cl.
  USPC .......................................................... 536/24.3
(58) Field of Classification Search
  None
  See application file for complete search history.

(56) References Cited

U.S. PATENT DOCUMENTS

| 6,291,170 B1 * | 9/2001 | Van Gelder et al. ......... 435/6.14 |
| 2003/0104432 A1 * | 6/2003 | Xu et al. ......................... 435/6 |

* cited by examiner

*Primary Examiner* — Kenneth R. Horlick
*Assistant Examiner* — David Thomas
(74) *Attorney, Agent, or Firm* — Servilla Whitney LLC (57) ABSTRACT

Compositions and methods are provided for amplifying nucleic acid molecules. The nucleic acid molecules can be used in various research and diagnostic applications, such as gene expression studies involving nucleic acid microarrays.

5 Claims, 5 Drawing Sheets

METHODS AND KITS FOR NUCLEIC ACID AMPLIFICATION

CROSS-REFERENCE TO RELATED APPLICATIONS

This application is a divisional of U.S. application Ser. No. 11/714,989, filed Mar. 6, 2007, which is a continuation of U.S. application Ser. No. 11/269,021, filed Nov. 8, 2005, now abandoned.

FIELD OF THE INVENTION

The present invention relates generally to compositions and methods for amplifying nucleic acid molecules.

BACKGROUND OF THE INVENTION

Microarray technology has become a powerful tool for generating and analyzing gene expression profiles. Microarray expression analysis, however, generally demands large amounts of RNA that are often not available (see Wang et al., BioTechniques 34:394 (2003)). Several RNA amplification techniques have been developed to overcome this problem. These techniques, however, generally suffer from a phenomenon known as amplification bias (see, e.g., U.S. Pat. No. 6,582,906). In these cases, the amplified population of RNA molecules does not proportionally represent the population of RNA molecules existing in the original sample.

For example, in the method disclosed by Eberwine and colleagues (see, e.g., U.S. Pat. Nos. 5,545,522; 5,716,785; 5,891,636; 5,958,688; and 6,291,170), a compound oligonucleotide is utilized for the amplification, wherein the compound oligonucleotide is provided with both a T7 promoter and a primer. A cDNA copy is created of an initial mRNA transcript using the compound oligonucleotide, with subsequent second strand synthesis to create a cDNA that is double stranded. RNA amplification is conducted via the promoter portion of the compound oligonucleotide, with transcription proceeding off of the cDNA's second strand. Since the second strand is used for transcription, the Eberwine method produces amplified RNA that is antisense to the initial mRNA sequence (termed cRNA or aRNA).

The Eberwine method, however, introduces a 3' bias during each of its steps due to the incomplete processivities (i.e., the inability of an enzyme to remain attached to a nucleic acid molecule) of the enzymes utilized and the positioning of the RNA polymerase promoter (see, e.g., U.S. Pat. No. 6,582,906 and U.S. Patent Publication No. US2003/0104432). For example, the compound oligonucleotide used to produce first strand cDNA places the promoter at the 5' end of the cDNA, which corresponds to the 3' end of the message. This coupled with the inability of RNA polymerase to complete transcription of some templates (due perhaps to long polyA tail regions or interference from secondary and tertiary structures in the template) can result in a 3' bias in the amplified antisense RNA population. In addition, if second strand cDNA synthesis by DNA polymerase is incomplete, these cDNAs will lack functional promoters, resulting in a reduced representation of the original RNA molecule (or possibly a complete absence) in the amplified population.

Applicants' copending patent applications U.S. patent application Ser. Nos. 10/979,052, 11/150,794 and 11/210,602, and International Application No. PCT/US2004/014325, each specifically incorporated herein by reference in its entirety, disclose methods for attaching or synthesizing RNA polymerase promoters onto the 3' ends of cDNA molecules. In vitro transcription is initiated by addition of RNA polymerase, resulting in the synthesis of sense RNA (sRNA) molecules having the same orientation as the original RNA molecules from which the cDNA molecules were synthesized. For downstream applications, such as gene expression studies, the sRNA molecules can be reverse transcribed into cDNA molecules or used in aRNA amplification reactions using the Eberwine method described above.

Reverse transcription of the sRNA molecules, however, provides no further amplification of the original nucleic acid sequences, limiting its use when small amounts of RNA are involved. Eberwine's aRNA method, while providing amplification, often results in large amounts of non-specific artifacts due to the use of a compound oligonucleotide containing an intact T7 promoter.

It would be desirable to provide methods and kits for synthesizing antisense RNA (asRNA) molecules directly from sRNA molecules which provides increased amplification with low amounts of non-specific artifacts.

SUMMARY OF THE INVENTION

Applicants have invented methods for the synthesis of asRNA molecules directly from sRNA molecules, wherein a partial RNA polymerase recognition sequence at the 3' ends of sRNA molecules is converted into a complete RNA polymerase recognition sequence and ultimately into a double stranded RNA polymerase promoter. Subsequent RNA transcription using an RNA polymerase that recognizes the double stranded RNA polymerase promoter results in the production of amplified asRNA molecules. Applicants have discovered that this method of promoter formation and amplification provides lower amounts of non-specific artifacts compared to traditional aRNA amplification methods involving intact promoter primers.

Accordingly, one aspect of the present invention is directed to a method for synthesizing at least one asRNA molecule directly from at least one sRNA molecule, comprising:

a) providing at least one sRNA molecule having a 5' end and a 3' end, said 3' end comprising a first nucleotide sequence corresponding to the partial 5' end of the template strand of a RNA polymerase recognition sequence;

b) annealing to the 3' end of said sRNA molecule a primer having a 5' end and a 3' end, said primer comprising a second nucleotide sequence corresponding to at the 5' end of the non-template strand of said RNA polymerase recognition sequence sufficient in length to anneal to said first nucleotide sequence corresponding to the partial 5' end of the template strand of said RNA polymerase recognition sequence;

c) extending the 3' end of said primer such that a double stranded RNA/DNA duplex is formed;

d) degrading at least the 3' portion of the RNA strand of said double stranded RNA/DNA duplex, thereby providing at least a partially single stranded DNA molecule having a single stranded 5' end, said 5' end comprising a third nucleotide sequence corresponding to the complete non-template strand of said RNA polymerase recognition sequence;

e) synthesizing at least a partially double stranded DNA molecule from said at least partially single stranded DNA molecule such that said third nucleotide sequence corresponding to the complete non-template strand of said RNA polymerase recognition sequence is converted into a double stranded RNA polymerase promoter; and f) initiating RNA transcription using an RNA polymerase which recognizes said double stranded RNA polymerase promoter, thereby synthesizing at least one asRNA molecule directly from at least one sRNA molecule.

In some embodiments, the at least partially double strand stranded DNA molecule is synthesized by performing second strand DNA synthesis with an exogenous primer. In other embodiments, the at least partially double strand stranded DNA molecule is synthesized by extending a remaining 5' portion of the RNA strand of the double stranded RNA/DNA duplex.

As described more fully below, the sRNA molecule can be provided by attaching one or more RNA polymerase promoters to the 3' end of a cDNA molecule, followed by one or more rounds of RNA transcription with RNA polymerases which recognizes the RNA polymerase promoters. The cDNA molecule can be provided by contacting a RNA molecule with a primer having a 5' extension comprising a fourth nucleotide sequence corresponding to the complement of the first nucleotide sequence in the presence of a reverse transcriptase. Such reverse transcription primers include oligodT primers, random primers or combinations thereof. Upon reverse transcription of the RNA molecule and subsequent RNA transcription of the resulting cDNA molecule, the fourth nucleotide sequence of the reverse transcription primer becomes the first nucleotide sequence at the 3' end of the sRNA molecule.

Applicants have also invented kits for the synthesis of asRNA molecules directly from sRNA molecules, wherein a partial RNA polymerase recognition sequence at the 3' ends of sRNA molecules is converted into a complete RNA polymerase recognition sequence and ultimately into a double stranded RNA polymerase promoter.

Accordingly, another aspect of the present invention is directed to a kit for synthesizing one or more asRNA molecules directly from a sRNA molecule, comprising: one or more primers comprising a nucleotide sequence corresponding to at least a portion of the 5' end of the non-template strand of an RNA polymerase recognition sequence; and instructional materials for synthesizing asRNA molecules directly from sRNA molecules using said primer. In some embodiments, the kit further comprises reagents and instructional materials for synthesizing sRNA molecules from which asRNA molecules can be directly synthesized.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

DETAILED DESCRIPTION OF THE INVENTION

The methods of the present invention utilize routine techniques in the field of molecular biology. Basic texts disclosing general molecular biology methods include Sambrook et al., Molecular Cloning, A Laboratory Manual (3d ed. 2001) and Ausubel et al., Current Protocols in Molecular Biology (1994).

The present invention relates to methods and kits for amplifying nucleic acid molecules. The terms "nucleic acid molecule", "RNA molecule", "sRNA molecule", "asRNA molecule", "aRNA molecule, "cRNA molecule", "DNA molecule", and "cDNA molecule" are each intended to cover a single molecule, a plurality of molecules of a single species, and a plurality of molecules of different species.

The methods of the present invention generally comprise converting a partial RNA polymerase recognition sequence at the 3' ends of sRNA molecules into a complete RNA polymerase recognition sequence and ultimately into a double stranded RNA polymerase promoter. Subsequent RNA transcription using an RNA polymerase that recognizes the double stranded RNA polymerase promoter results in the production of amplified asRNA molecules. Such asRNA molecules find utility in various downstream applications, including gene expression studies involving nucleic acid microarrays. The methods of present invention are particularly suited for amplification of RNA from small numbers of cells, including single cells, which can be purified from complex cellular samples using, e.g., micromanipulation, fluorescence-activated cell sorting (FACS) and laser microdissection techniques (see Player et al., Expert Rev. Mol. Diagn. 4:831 (2004)).

The term "RNA polymerase recognition sequence" is intended to cover both single stranded and double stranded nucleotide sequences. When in single stranded form, the nucleotide sequence corresponds to the template or non-template strand of a double-stranded RNA polymerase promoter. "Template strand" refers to a strand of nucleic acid on which a complementary copy is synthesized from nucleotides or nucleotide analogs through the activity of a template-dependent nucleic acid polymerase. "Non-template strand" refers to the nucleic acid strand that is complimentary to the template strand. When in double stranded form, the nucleotide sequences correspond to both the template and non-template strands of a double-stranded RNA polymerase promoter.

Any method for producing sRNA molecules can be used as the source of such molecules in the methods of the present invention, so long as their 3' ends comprise a nucleotide sequence corresponding to the partial 5' end of the template strand of a RNA polymerase recognition sequence. For example, the sRNA molecules can be produced by in vitro transcription of cDNA molecules containing one or more RNA polymerase promoters at their 3' ends. Such methods include those disclosed in Applicants' copending patent applications U.S. patent Ser. Nos. 10/979,052, 11/150,794 and 11/210,602, and International Application No. PCT/US2004/014325, as well as in U.S. patent application Ser. Nos. 10/805,171, 10/302,675, 10/206,613 and 10/075,335 (each of which is specifically incorporated herein by reference in its entirety). Commercial kits are also available for the production of sRNA molecules, such as, e.g., the SMART™ mRNA Amplification Kit (Clontech, Mountain View, Calif.) and the ArrayIt MiniAmp mRNA Amplification Kit (ArrayIt, Sunnyvale, Calif.).

To ensure that the 3' ends of the sRNA molecules comprise a nucleotide sequence corresponding to the partial 5' end of the template strand of a RNA polymerase recognition sequence, the cDNA molecules are provided by reverse transcription of an RNA molecule of interest with a primer having a 5' extension comprising a nucleotide sequence corresponding to the partial 3' end of the non-template strand of the RNA polymerase recognition sequence. The length of the 5' extension generally ranges from about 2 to about 19 nucleotides in length, preferably from about 8 to about 12 nucleotides in length.

Upon reverse transcription of the RNA molecule of interest and subsequent in vitro transcription of the resulting cDNA molecule, the nucleotide sequence of the primer extension is converted into the 3' nucleotide sequence of the sRNA molecule corresponding to the partial 5' end of the template strand of the RNA polymerase recognition sequence. Any RNA polymerase recognition sequence can be used in the methods described herein, so long as it is specifically recognized by an RNA polymerase. Preferably, the RNA polymerase recognition sequence used is recognized by a bacteriophage RNA polymerase, such as T7, T3, or SP6 RNA polymerase. An exemplary T7 RNA polymerase recognition sequence is TAATACGACTCACTATAGGG (SEQ ID NO: 1). An exemplary T3 RNA polymerase recognition sequence is AATTAACCCTCACTAAAGGG (SEQ ID NO: 2). An exemplary SP6 RNA polymerase recognition sequence is AATTTAAG-GTGACACTATAGAA (SEQ ID NO: 3).

Figure 1A:
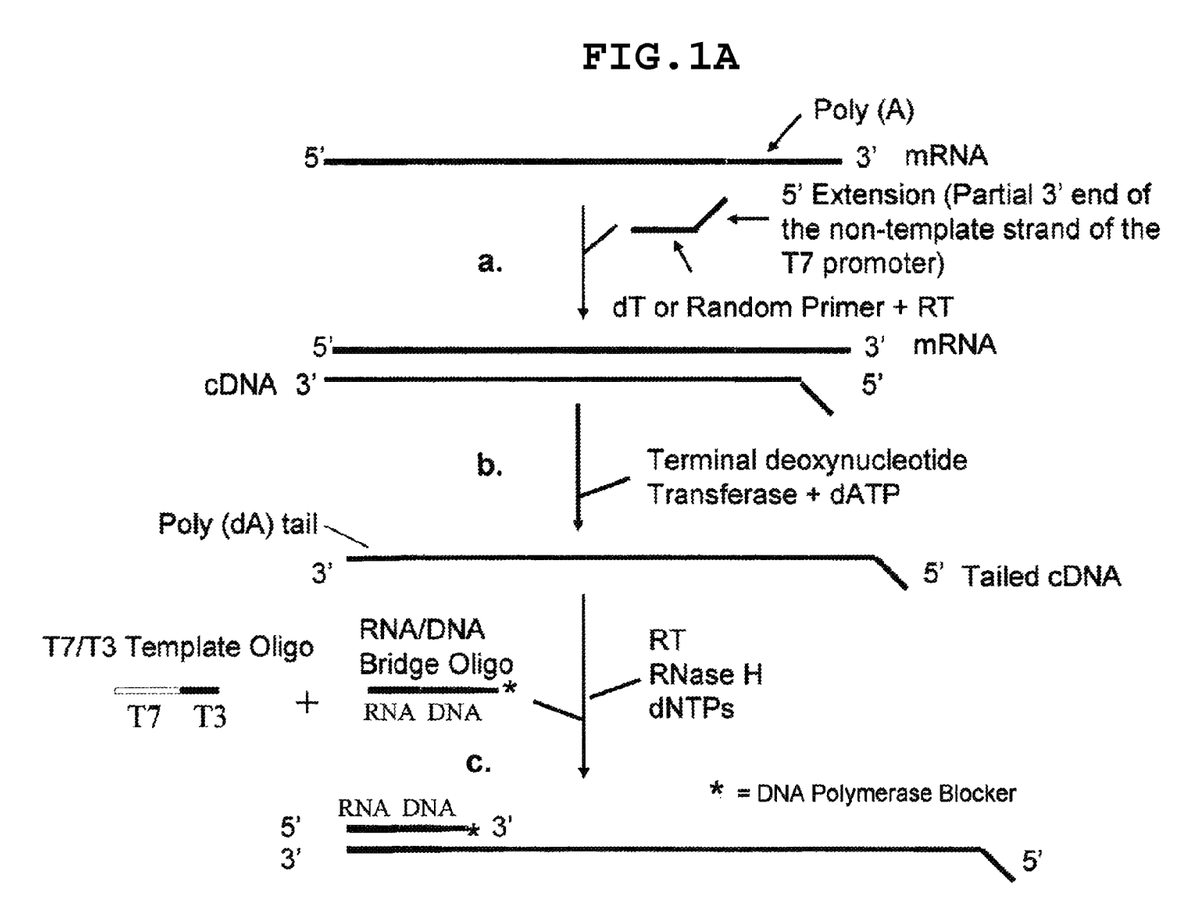
FIGS. 1A-1C are a schematic representation that depicts an embodiment for synthesis of sRNA molecules according to the methods of the present invention.
Figure 1B:
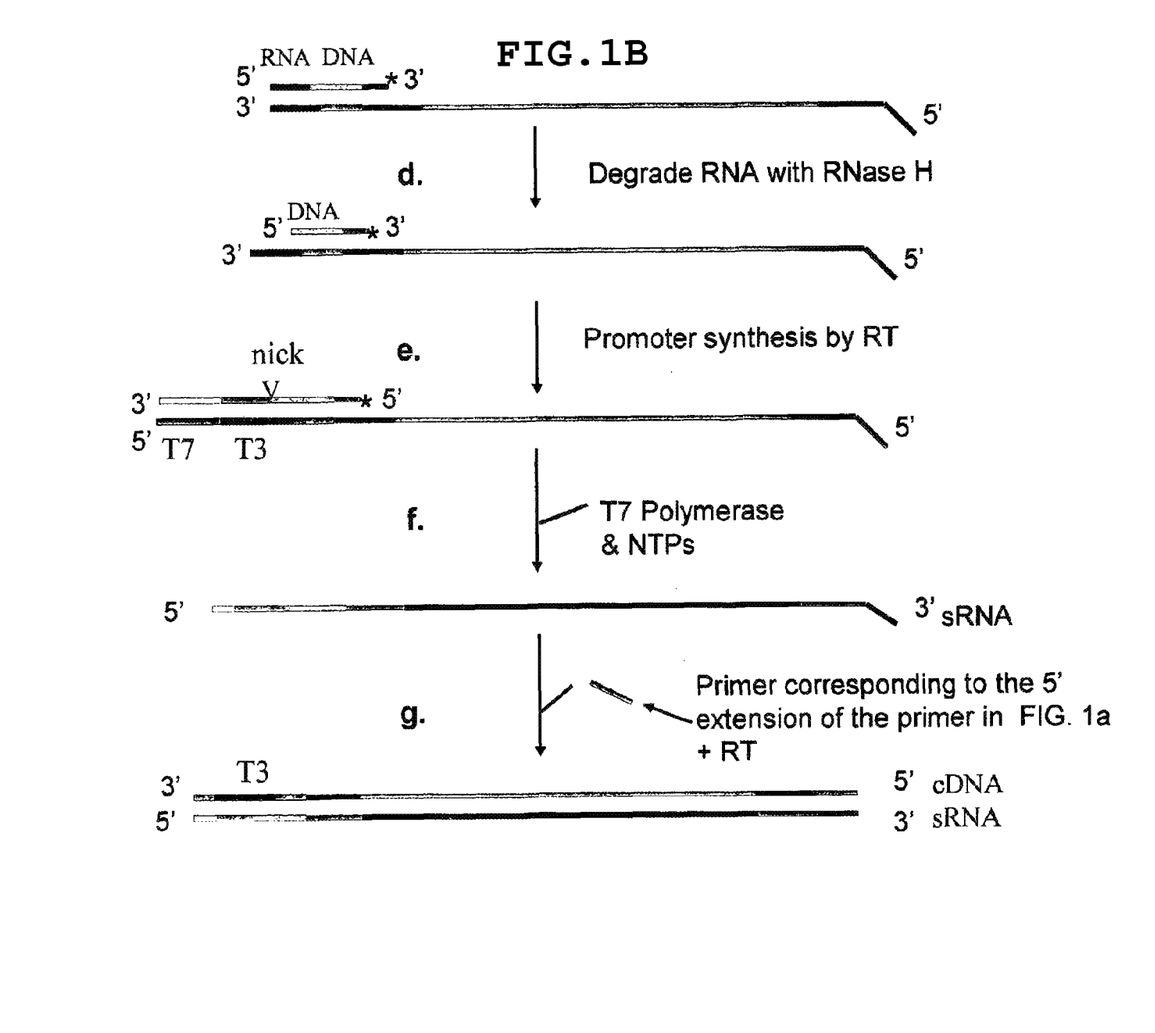
Figure 1C:
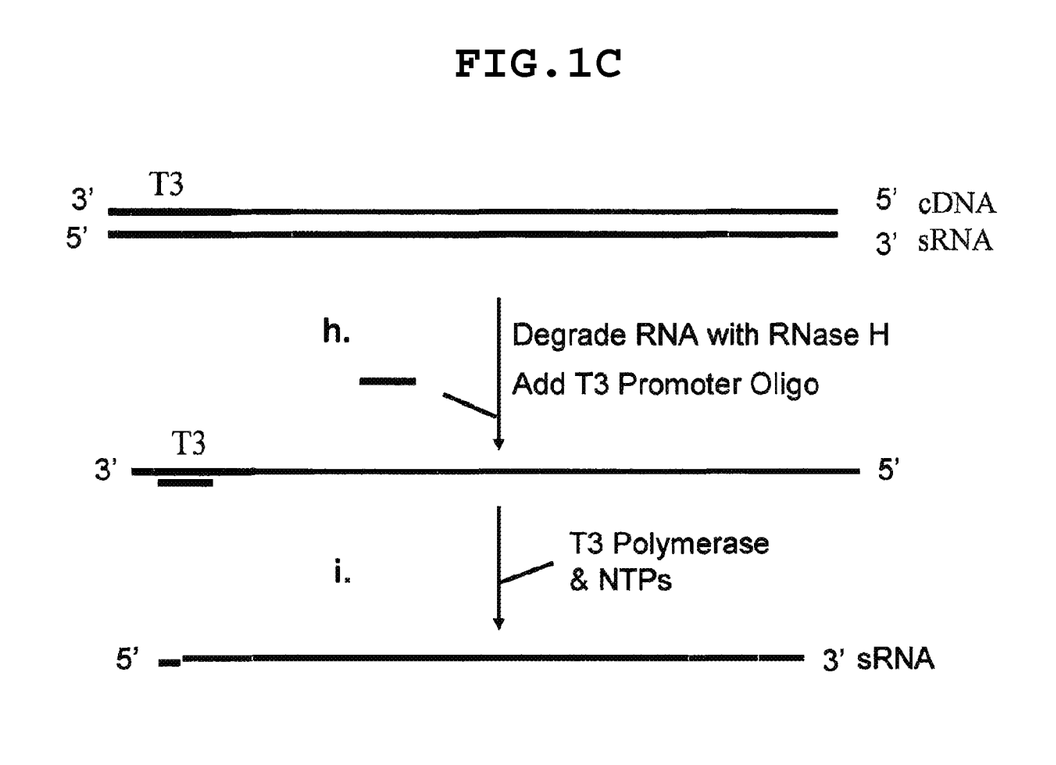

For example, with reference to FIGS. 1A-1C (an embodiment previously described in Applicants' copending U.S. patent application Ser. No. 11/210,602, specifically incorporated herein by reference in its entirety), RNA molecules (e.g., mRNA, hnRNA, rRNA, tRNA, miRNA, snoRNA, non-coding RNAs) from a source of interest are reversed transcribed into cDNA molecules using a primer having the required 5' extension (in the case of FIGS. 1A-1C, the partial 5' end of the template strand of the T7 promoter) (see FIG. 1A, step a). The RNA may be obtained from any tissue or cell source, including virion, prokaryotic, and eukaryotic sources found in any biological or environmental sample. Preferably, the source is eukaryotic tissue, more preferably mammalian tissue, even more preferably human tissue.

Any reverse transcriptase can be used in the reverse transcription reaction, including thermostable and RNase H$^-$ reverse transcriptases. Preferably, a RNase H$^-$ reverse transcriptase is used. Numerous methods and commercial kits for the synthesis of cDNA molecules are well known in the art. Examples include the Superscript™ Double Strand cDNA Synthesis kit (Invitrogen, Carlsbad, Calif.), the Array 50™, Array 350™ and Array 900™ Detection kits (Genisphere, Hatfield, Pa.), and the CyScribe™ Post-Labelling kit (Amersham, Piscataway, N.J.).

Suitable reverse transcription primers containing the required 5' extension include single stranded oligodeoxynucleotides comprising an oligodT tail at their 3' ends, the tail generally ranging from about 10 to about 30 nucleotides in length, preferably from about 17 to about 24 nucleotides in length, which anneal to RNA containing a 3' polyA tail (e.g., mRNA). If the RNA of interest does not naturally contain a 3' polyA tail (e.g., miRNA), a polyA tail can be attached to the RNA molecules using poly(A) polymerase (PAP) in the presence of ATP. PolyA tailing kits are commercially available and include, e.g., the Poly(A) Tailing Kit (Ambion, Austin, Tex.). Three-primer blocked RNAs can be enzymatically treated to allow tailing using, e.g., calf intestinal alkaline phosphatase or RNase 3.

Alternatively, the reverse transcription reaction can be initiated using a random primer having the required 5' extension, the random nucleotide portion generally ranging from about 4 to about 20 nucleotides in length, preferably from about 6 to about 9 nucleotides in length, which anneals to various positions along the length of each original mRNA transcript. One of ordinary skill in the art will recognize that the use of a random primer can ultimately result in the production of sRNA molecules that are better representative of the entire length of each original mRNA transcript than those produced using an oligodT primer. Additionally, the use of a random primer to generate cDNA in the initial steps of the disclosed methods means that RNA that would normally be exempt from amplification, such as degraded RNA or RNA derived from bacteria, can be used to produce amplified sRNA molecules.

In some embodiments, the 3' terminal nucleotide of the reverse transcription primer (oligodT primer, random primer, or both) is a nucleotide or nucleotide analog that is not a substrate for terminal deoxynucleotide transferase but can be extended by reverse transcriptase, such as a ribonucleotide. Such primers are not extendable with terminal deoxynucleotidyl transferase (TdT), and thus will not be tailed and amplified in the steps shown in FIGS. 1b-1f.

Following first strand cDNA synthesis, the resulting first round cDNA molecules are generally purified (see FIG. 1A, step b). While not degrading the RNA prior to cDNA purification is preferred, cDNA that has been purified following RNA degradation works equally well in the methods of the present invention. Any method that degrades RNA can be used, such as treatment with NaOH or RNase H (whether supplied in the form of a RNase H$^+$ reverse transcriptase or as a separate enzyme). Alternatively, the RNA can be left intact, with the first round cDNA molecules purified from RNA/cDNA duplexes. Numerous methods and kits exist for the purification of DNA molecules, including, e.g., the MinElute™ PCR Purification Kit (Qiagen, Valencia, Calif.). If a reverse transcription primer is used for first strand cDNA synthesis in which the 3' terminal nucleotide is a ribonucleotide, DNA purification can be omitted. This may reduce sample loss and increase amplification yield, which is particularly important when manipulating RNA from small numbers of cells.

Following first round cDNA purification, a single stranded oligodeoxynucleotide tail is generally attached to the 3' end of the cDNA molecules (see FIG. 1A, step b). The use of such oligodeoxynucleotide tails allows whole populations of nucleic acid molecules to be amplified, rather than just specific sequences. The oligodeoxynucleotide tail can be incorporated by any means that attaches deoxynucleotides to DNA. Preferably, the oligodeoxynucleotide tail is attached to the cDNA using terminal deoxynucleotidyl transferase, or other suitable enzyme, in the presence of appropriate deoxynucleotides. Preferably, the oligodeoxynucleotide tail is a homopolymeric tail (i.e., polydA, polydG, polydC, or polydT). Preferably, the oligodeoxynucleotide tail is a polydA tail, generally ranging from about 3 to greater than 500 nucleotides in length, preferably from about 20 to about 100 nucleotides in length. Applicants have found that the use of a polydA tail reduces the number of artifacts resulting from non-specific amplification.

Following attachment of the single stranded oligonucleotide tail to the 3' ends of the cDNA molecules, a single stranded RNA/DNA composite bridge oligonucleotide comprising a 5' RNA portion and a 3' DNA portion is annealed to the 3' oligodeoxynucleotide tail (see FIG. 1A, step c). This is accomplished through complementary base pairing between the 3' oligodeoxynucleotide tail and at least a portion of the 3' DNA portion of the RNA/DNA composite bridge oligonucleotide. For example, if oligonucleotide tail is a polydA tail, the 3' DNA portion of the RNA/DNA composite bridge oligonucleotide will contain a series of thymidines at its 3' end, generally ranging from about 3 to greater than 50 nucleotides in length, preferably from about 10 to about 30 nucleotides in length. The particular deoxynucleotide sequence of the 3'

DNA portion of the RNA/DNA composite bridge oligonucleotide does not have to be perfectly complementary to the particular nucleotide sequence of the oligodeoxynucleotide tail at the 3' ends of the cDNA molecules, nor do their lengths need to match exactly, for the sequences to be considered complementary to each other. Those of skill in the art will recognize that what is required is that there be sufficient complementarity between the two sequences so that the RNA/DNA composite bridge oligonucleotide can anneal to the oligodeoxynucleotide tail at the 3' end of the cDNA molecules.

In some embodiments, rather than attaching a single stranded oligodeoxynucleotide tail to the 3' ends of the cDNA molecules, a single stranded RNA/DNA composite bridge oligonucleotide in which the DNA portion comprises random nucleotides is annealed to the cDNA molecules. Again, the use of such a random composite bridge oligonucleotide allows whole populations of nucleic acid molecules to be amplified, rather than just specific sequences. The random DNA portion of the composite oligonucleotide generally ranges from about 3 to greater than 50 nucleotides in length, preferably from about 6 to about 20 nucleotides in length. Only those bridge oligonucleotides that hybridize to the 3' ends of the cDNA molecules will result in the synthesis of functional RNA polymerase promoters as described below. Hybridization is preferably performed at about 37° C. to about 55° C., more preferably at 45° C. to about 50° C.

In addition to the 3' DNA portion (whether random or defined), the composite bridge oligonucleotide contains a 5' RNA portion which remains single stranded (i.e., unannealed) following the annealing of the 3' DNA portion of the composite bridge oligonucleotide to the 3' oligodeoxynucleotide tail. The 5' RNA portion generally ranges from about 3 to greater than 50 nucleotides in length, preferably from about 10 to about 30 nucleotides in length. Preferably, the particular sequence of the 5' RNA portion is not substantially homologous to any known nucleic acid sequence, nor is it substantially self-complementary or complementary to any portion of the single stranded RNA polymerase promoter template described below.

The RNA/DNA composite bridge oligonucleotide can be blocked at its 3' end if desired, such that it is not extendable with a DNA polymerase (see FIG. 1A, step c). As such, the addition of reverse transcriptase with both RNA-dependent and DNA-dependent DNA polymerase activity (e.g., MMLV reverse transcriptase, AMV reverse transcriptase, RBst DNA polymerase (Epicentre Technologies, Madison, Wis.)) and dNTPs extends the single stranded 3' oligonucleotide tail at the 3' ends of the cDNA molecules such that the RNA portion of the bridge oligonucleotide becomes a double stranded RNA/DNA duplex, but does not catalyze the synthesis of second strand cDNA (see FIG. 1A, step c). The RNA/DNA composite bridge oligonucleotide can be blocked by any means that renders it incapable of being extended with DNA polymerase, such as by including terminal blocking groups, compounds, or moieties either attached during or after synthesis. Preferably, the RNA/DNA composite bridge oligonucleotide is blocked with a 3' amino modifier, a 3' deoxyterminator, or a 3' dideoxyterminator. A suitable blocker should not be restricted to any of those described herein and can include any moiety that will prevent a DNA polymerase from extending the 3' terminus of the RNA/DNA composite bridge oligonucleotide.

Following extension of the 3' oligonucleotide tail to form a RNA/DNA duplex, the RNA portion of the duplex (i.e., the RNA portion of the bridge oligonucleotide) is degraded with RNase to expose a 3' single stranded DNA tail on the cDNA molecules (see FIG. 1B, step d). Preferably, the RNase is RNase H, although other RNases, such as RNase 1 and RNase A can be used. The RNase can be provided as part of the reverse transcriptase or as a separate enzyme. The RNase is preferably added at substantially the same time as the reverse transcriptase and the bridge oligonucleotide (see FIG. 1A, step c).

Following degradation of RNA portion of the RNA/DNA duplex, a single stranded RNA polymerase promoter template is attached to the exposed 3' single stranded DNA tail on the cDNA molecules (see FIG. 1B, step e). This is accomplished through complementary base pairing between the exposed 3' single stranded DNA tail and a complementary series of nucleotides present at the 3' end of the single stranded promoter template, generally ranging from about 3 to greater than 50 nucleotides in length, preferably from about 10 to about 30 nucleotides in length.

The single stranded promoter template contains at its 5' end at least one RNA polymerase recognition sequence. The promoter template can be composed of RNA and/or DNA, and can be blocked or unblocked at its 3' end. When composed of both RNA and DNA, the 3' portion of the promoter template that hybridizes to the exposed DNA tail on the cDNA molecules is preferably DNA, while the 5' unhybridized portion is RNA. For performing multiple rounds of sRNA synthesis, the promoter template preferably contains at least a second different RNA polymerase recognition sequence 3' to the first recognition sequence (i.e., a "tandem promoter template"; see FIG. 1A, step c) (see Applicants' co-pending U.S. patent application Ser. No. 11/150,794, specifically incorporated herein by reference in its entirety). Again, any RNA polymerase recognition sequence can be used, so long as it is specifically recognized by an RNA polymerase. Preferably, the RNA polymerase recognition sequence(s) used is recognized by a bacteriophage RNA polymerase, such as T7, T3, or SP6 RNA polymerase. The RNA polymerase promoter template is preferably added at substantially the same time as the reverse transcriptase, bridge oligonucleotide and RNase (e.g., in the same reaction vessel) (see FIG. 1A, step c), although each of the reactions can be performed separately.

Following attachment, the reverse transcriptase from FIG. 1A, step c, having DNA-dependant DNA polymerase activity, extends the exposed 3' single stranded DNA tail on the cDNA molecules and converts the single stranded promoter template into one or more double stranded RNA polymerase promoters (in the case of FIG. 1, T7 and T3 promoters) (see FIG. 1B, step e). Even unblocked promoter templates are not extended during the reaction because reverse transcriptase lacks 5'→3' exonuclease and strand displacement activities. Alternatively, or in addition, to reverse transcriptase, a DNA polymerase, such as T4 DNA polymerase, T7 DNA polymerase, or Sequenase.TM. (USB Corporation, Cleveland, Ohio), all of which lack 5'→3' exonuclease and strand displacement activities, can be used to extend the exposed 3' single stranded DNA tail on the cDNA molecules and convert the single stranded promoter template into a double stranded RNA polymerase promoter. Klenow enzyme has even been shown in the present system to convert the promoter template into a RNA polymerase promoter without extending the template when added near the end of the reverse transcriptase/RNase promoter synthesis reaction(s) (e.g., about 5 min to about 15 min before the completion of promoter synthesis). The use of such DNA polymerases may prevent or correct incorporation errors associated with the use of reverse transcriptase alone.

To further ensure that unblocked promoter templates are not extended during the promoter synthesis reaction(s), a nucleotide extension can be included at the 3' end of an unblocked single stranded promoter template. This 3' terminal nucleotide extension, downstream of the complementary 3' series of deoxynucleotides used to attach the promoter template to the exposed 3' single stranded DNA tail on the cDNA molecules, comprises a series of nucleotides identical to the 5' end of the remaining DNA portion of bridge oligonucleotide, generally ranging from about 3 to about 10 nucleotides in length. As such, the 3' extension, which would bind to the cDNA molecules but for the presence of the remaining DNA portion of bridge oligonucleotide, functions to prevent access to the gap or nick present between the promoter template and the remaining DNA portion of the bridge oligonucleotide during promoter synthesis (see FIG. 1e). Thus, any potential strand displacement during promoter synthesis is prevented as long as a DNA polymerase incapable of degrading the 3' nucleotide extension is used in the synthesis reactions(s) (e.g., Klenow exo⁻).

In some embodiments, rather than enzymatically synthesizing a double stranded RNA polymerase promoter from a single stranded promoter template, a double stranded RNA polymerase promoter having a template strand and a non-template strand is attached to the 3' ends of the first round cDNA molecules by DNA ligation (see Applicant's co-pending International Patent Application No. PCT/US2004/014325, specifically incorporated herein by reference in its entirety). The double stranded RNA polymerase promoter contains at its 5' end (relative to the non-template strand) at least one RNA polymerase recognition sequence. For performing multiple rounds of sRNA synthesis, the double stranded RNA polymerase promoter preferably contains at least a second different RNA polymerase recognition sequence 3' to the first recognition sequence (i.e., a "tandem promoter template") (see Applicants' co-pending U.S. patent application Ser. No. 11/150,794, specifically incorporated herein by reference in its entirety). Attachment of the promoter is facilitated by complementary base pairing between the exposed 3' single stranded DNA tail on the cDNA molecules and an overhang sequence at the 3' end of the non-template strand of the double stranded RNA polymerase promoter that contains a complementary series of nucleotides, generally ranging from about 3 to greater than 50 nucleotides in length, preferably from about 10 to about 30 nucleotides in length. Once properly positioned, the double stranded promoter is attached to the cDNA molecule by ligation of the 5' end of the template strand of the promoter to the 3' end of the exposed single stranded DNA tail. Any DNA ligase can be used in the ligation reaction. Preferably, the DNA ligase is T4 DNA ligase.

When performing a promoter synthesis reaction (see FIG. 1B, step e), second strand cDNA can be optionally synthesized by using a random primer. The random primer will anneal at various positions along the first strand cDNA and be extended by any DNA-dependant DNA polymerase activity during promoter synthesis. The various second strand cDNA fragments can be optionally ligated together to form a single second strand cDNA molecule. Such second strand cDNA molecules may stabilize (i.e., remove secondary and tertiary structure) the first strand cDNA during in vitro transcription, resulting in a higher yield of sRNA molecules.

Following synthesis or attachment of double stranded RNA polymerase promoter, in vitro transcription is initiated by the addition of ribonucleotides and a RNA polymerase that recognizes the promoter (see FIG. 1B, step f). This provides sRNA molecules having a partial RNA polymerase recognition sequence at their 3' ends. If a tandem promoter template was attached to the cDNA molecules (see FIG. 1B, step e), in vitro transcription is preferably initiated using a RNA polymerase that recognizes the first 5' promoter (in the case of FIG. 1, the T7 promoter) (see FIG. 1B, step f). This facilitates second round sRNA synthesis described in further detail below. Methods and kits for performing in vitro transcription are well known in the art and include the MEGAscript™ Transcription Kit (Ambion) and the AmpliScribe™ High Yield Transcription Kits (Epicentre Technologies).

Additional rounds of sRNA synthesis can be performed by reverse transcribing the resulting first round sRNA molecules (i.e., second round cDNA molecules) and re-attaching or re-synthesizing a double stranded RNA polymerase promoter onto the second-round cDNA molecules as just described (see FIGS. 1A-1B, steps a-e), followed by a second round of in vitro transcription with RNA polymerase.

If, however, a tandem promoter template was attached to the first round cDNA molecules (see FIG. 1B, step e), and in vitro transcription initiated using a RNA polymerase that recognizes the first 5' promoter (see FIG. 1B, step f), additional rounds of sRNA synthesis can be performed without the need for re-attachment or re-synthesis of the double stranded RNA polymerase promoter (see Applicants' co-pending U.S. patent application Ser. No. 11/150,794, specifically incorporated herein by reference in its entirety).

Briefly, the first round sRNA molecules are subjected to a second round of synthesis by first reverse transcribing the sRNA molecules into first strand cDNA molecules (i.e. second round cDNA synthesis) using a primer comprising a nucleotide sequence complementary to the RNA polymerase recognition sequence at the 3' ends of the first round sRNA molecules (i.e., "corresponding" to the specific nucleotide sequence of the 5' extension of the reverse transcription primer used for first round cDNA synthesis in the step shown in FIG. 1A, step a) (see FIG. 1B, step g). This ensures that the second round sRNA molecules also contain the same partial RNA polymerase recognition sequence at their 3' ends as the first round sRNA molecules.

Following second round cDNA synthesis, the RNA strand is degraded using NaOH or preferably RNase H prior to optional purification of the first strand cDNA molecules (see FIG. 1C, step h). Similarly, an RNase H⁺ reverse transcriptase can be used, such as MMLV.

Following RNA degradation, a single stranded promoter oligonucleotide complementary to the second different 3' RNA polymerase recognition sequence is annealed to the second round cDNA molecules through complementary base pairing (see FIG. 1C, step h). This base pairing forms a second RNA polymerase promoter, from which a second round of in vitro transcription (i.e., second round sRNA molecules) is initiated by the addition of ribonucleotides and a RNA polymerase that recognizes the second promoter (in the case of FIG. 1, the T3 promoter) (see FIG. 1C, step i). This provides second round sRNA molecules having a partial RNA polymerase recognition sequence at their 3' ends. By incorporating additional different RNA polymerase recognition sequences into the promoter template, additional rounds of sRNA synthesis can be performed as described (e.g., third round sRNA molecules, etc.). Further, by heat inactivating all enzymes between steps or before addition of RNA polymerase, using methods familiar to one skilled in the art, linear, rather than exponential, amplification can be maintained. Such linear amplification is better suited for various downstream applications, such as gene expression studies.

In some embodiments, rather than inactivating the reverse transcriptase following second round cDNA synthesis and annealing a single stranded promoter oligonucleotide complementary to the second different RNA polymerase recognition sequence, the RNA strand is degraded using Rnase H and the tandem promoter is regenerated by the binding of excess single stranded tandem promoter template (from the first round) to the 3' ends of the second round cDNA molecules and the DNA-dependent DNA polymerase activity of the still-active reverse transcriptase (see Applicants' co-pending U.S. patent application Ser. No. 11/150,794, specifically incorporated herein by reference in its entirety). A second round of in vitro transcription can then be initiated by the addition of an RNA polymerase that recognizes either the first or second promoter. Again, the reverse transcriptase is generally heat inactivated just prior to addition of RNA polymerase to maintain the linearity of the amplification. Those of skill in the art will recognize that the single stranded promoter template in these embodiments need not contain two RNA polymerase recognition sequences in tandem. Rather, the promoter template can contain a single RNA polymerase recognition sequence, which can be used in place of the tandem promoter template to produce first and second round sRNA molecules.

Figure 2:
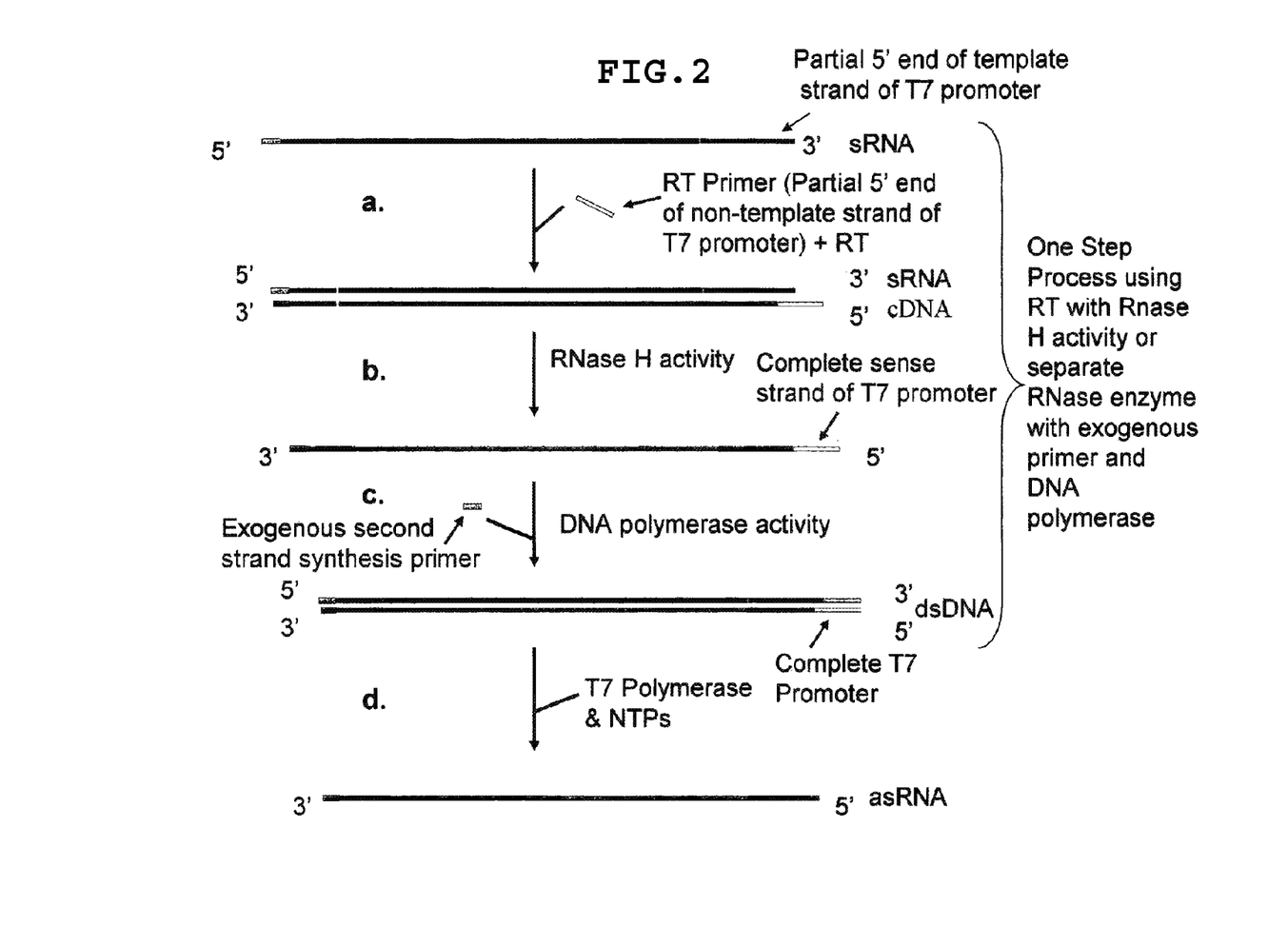
FIG. 2 is a schematic representation that depicts an embodiment for synthesis of asRNA molecules directly from sRNA molecules according to the methods of the present invention.

The sRNA molecules resulting from the above-described processes (or any other suitable process) can then be converted into templates for the direct synthesis of asRNA molecules by first reverse transcribing them with a primer comprising a nucleotide sequence corresponding to at least the 5' end of the non-template strand of the RNA polymerase recognition sequence (see FIG. 2, step a). The nucleotide sequence is of sufficient length to anneal to the nucleotide sequence at the 3' ends of the sRNA molecules corresponding to the partial 5' end of the template strand of the RNA polymerase recognition sequence, preferably from about 2 to about 19 nucleotides in length, preferably from about 8 to about 12 nucleotides in length.

Extension of the primer with reverse transcriptase produces a double stranded RNA/DNA duplex, the DNA portion of which now contains a nucleotide sequence corresponding to the complete non-template strand of the RNA polymerase recognition sequence at its 5' end (see FIG. 2, step a). At least the 3' portion of the RNA strand of the RNA/DNA duplex is degraded (see FIG. 2, step b), thereby providing at least a partially single stranded DNA molecule having a single stranded 5' end comprising a nucleotide sequence corresponding to the complete non-template strand of the RNA polymerase recognition sequence.

The RNA strand of the RNA/DNA duplex can be substantially completely degraded using a RNase enzyme separate from reverse transcriptase, such as RNase H (see FIG. 2, step b). Addition of an exogenous primer in the presence of a DNA polymerase produces a double strand stranded DNA molecule such that the nucleotide sequence at the 5' end of the first DNA strand corresponding to the complete non-template strand of said RNA polymerase recognition sequence is converted into a double stranded RNA polymerase promoter (see FIG. 2, step c).

The exogenous primer will comprise a nucleotide sequence of sufficient complementarity such that it anneals to the first DNA strand, preferably to the 3' region of the first DNA strand. More preferably, the exogenous primer anneals to the 3' most nucleotides of the first DNA strand. This ensures that most or all of the information present in each sRNA molecule or a particular sRNA molecule is captured during second strand DNA synthesis.

The exogenous primer can comprise any nucleotide sequence as long as it is complementary to a sequence of the first DNA strand known to the end-user. This sequence can either be naturally occurring or can be engineered by processes such as, e.g., those described above. For example, if an RNA/DNA composite bridge oligonucleotide was used as shown in FIG. 1A, step c, the exogenous primer can comprise a nucleotide sequence corresponding to the complement of at least a portion of the DNA portion of the bridge oligonucleotide, as shown in FIG. 2, step c. If a polydA tail was attached to the cDNA molecules as shown in FIG. 1A, step b (or in a similar method), the exogenous primer can comprise a series of thymidines of sufficient length to anneal to the first DNA strand in the step shown in FIG. 2, step c. Alternatively, the exogenous primer can comprise a naturally occurring gene-specific sequence, such that gene-specific asRNA molecules can be produced by in vitro transcription in the step shown in FIG. 2, step d.

In the in vitro transcription reaction, addition of ribonucleotides and a RNA polymerase that recognizes the promoter formed in the step shown in FIG. 2, step c results in the synthesis of asRNA molecules directly from sRNA molecules (see FIG. 2, step d), thereby providing an additional round of RNA amplification.

Alternatively, the RNA strand of the RNA/DNA duplex can be partially degraded using a reverse transcriptase having RNAse activity, such as, e.g., AMV reverse transcriptase or MMLV RNase $H^+$, without the addition of a separate RNase enzyme. In this one-step embodiment, the RNase activity of the reverse transcriptase degrades the RNA template strand essentially while synthesizing the complementary cDNA strand, thereby leaving a remaining portion of the RNA strand which can serve as a primer for second strand DNA synthesis. Again, addition of ribonucleotides and a RNA polymerase that recognizes the resulting promoter results in the synthesis of asRNA molecules directly from sRNA molecules, providing an additional round of RNA amplification.

The resulting asRNA molecules may represent up to a billion-fold amplification of each target RNA and can be used directly in gene expression studies. For example, the in vitro transcription reaction (see FIG. 2, step d) can be performed in the presence of detectably labeled nucleotides, such as fluorescently labeled nucleotides, to produce directly labeled asRNA molecules. Such nucleotides include nucleotides labeled with Cy3 and Cy5.

In alternative embodiments, the asRNA molecules are labeled indirectly following their synthesis. For example, in vitro transcription reaction can be performed in the presence amino allyl nucleotides (e.g., amino allyl UTP), followed by coupling to a NHS ester label (e.g., biotin, Cy dye).

In some embodiments, labeled cDNA molecules are synthesized rather than asRNA molecules. For example, the reverse transcription reaction shown in FIG. 2, step a can be performed in the presence of detectably labeled nucleotides, such as fluorescently labeled nucleotides (e.g., Cy3 and Cy5 labeled nucleotides), to produce directly labeled cDNA molecules, or the reaction can be performed in the presence amino allyl nucleotides (e.g., amino allyl UTP), followed by coupling to a NHS ester label (e.g., biotin, Cy dye), to produce indirectly labeled cDNA molecules.

Alternatively, the reverse transcription primer used in FIG. 2, step a can comprise a capture nucleotide sequence at its 5' end in addition to the nucleotide sequence necessary to anneal to the nucleotide sequence at the 3' ends of the sRNA molecules. Any defined nucleotide sequence can function as the capture nucleotide sequence, generally ranging from about 10 to about 100 nucleotides in length, preferably from about 25 to about 35 nucleotides in length. Preferably, the capture nucleotide sequence shares no significant homology with any known gene sequence.

The capture nucleotide sequence becomes incorporated into the cDNA molecules during the reverse transcription reaction shown in FIG. 2, step a. The resulting capture nucleotide sequence-containing cDNA molecules can be labeled indirectly using, e.g., 3DNA™ dendrimer technology (Genisphere, Hatfield, Pa.). The surfaces of these dendrimers comprise multiple nucleotide sequences complementary to the capture nucleotide sequence, as well as multiple attachment sites for labeled (e.g., Cy dye) oligonucleotides. Such dendritic nucleic acid reagents are further described in Nilsen et al., J. Theor. Biol., 187:273 (1997); Stears et al., Physiol. Genomics, 3:93 (2000); and U.S. Pat. Nos. 5,175,270; 5,484,904; 5,487,973; 6,072,043; 6,110,687; and 6,117,631, each of which is specifically incorporated herein by reference in its entirety.

The labeled asRNA and cDNA molecules are useful as reagents for gene expression studies. The labeled molecules can be annealed to a nucleic acid microarray containing complementary polynucleotides (e.g., probes). As used herein, "microarray" is intended to include any solid support containing nucleic acid probes, including slides, chips, membranes, beads, and microtiter plates. Examples of commercially available microarrays include the GeneChip® microarray (Affymetrix, Santa Clara, Calif.), CodeLink™ microarray (Amersham Biosciences, Piscataway, N.J.), Agilent (Palo Alto, Calif.) Oligo microarray, and OciChip™ microarray (Ocimum Biosolutions, Indianapolis, Ind.). If the asRNA and cDNA molecules are labeled indirectly, they can be labeled either prior to or following microarray hybridization.

The methods and compositions of the present invention can be conveniently packaged in kit form. Such kits can be used in various research and diagnostic applications. For example, methods and kits of the present invention can be used to facilitate a comparative analysis of expression of one or more genes in different cells or tissues, different subpopulations of the same cells or tissues, different physiological states of the same cells or tissue, different developmental stages of the same cells or tissue, or different cell populations of the same tissue. Such analyses can reveal statistically significant differences in the levels of gene expression, which, depending on the cells or tissues analyzed, can then be used to facilitate diagnosis of various disease states.

A wide variety of kits may be prepared according to present invention. For example, a kit may include one or more primers comprising a nucleotide sequence corresponding to at least a portion of the 5' end of the non-template strand of a RNA polymerase recognition sequence; and instructional materials for synthesizing asRNA molecules directly from sRNA molecules using said primer.

In addition, or alternatively, the kit can include reagents and instructional materials for synthesizing sRNA molecules from which asRNA molecules can be directly synthesized. For example, the kit may include one or more reverse transcription primers having a 5' extension comprising a nucleotide sequence corresponding to the partial 3' end of the non-template strand of a RNA polymerase recognition sequence; a single stranded promoter template comprising at least one RNA polymerase recognition sequence; a single stranded RNA/DNA composite bridge oligonucleotide comprising a RNA sequence 5' of a DNA sequence; and instructional materials for synthesizing sRNA molecules from which asRNA molecules can be directly synthesized.

For performing additional rounds of sRNA synthesis, the kit can further include one or more second round reverse transcription primers comprising a nucleotide sequence corresponding to the nucleotide sequence of the 5' extension of a first round reverse transcription primer or primers; and a single stranded promoter oligonucleotide complementary to a second RNA polymerase recognition sequence of the promoter template and the appropriate instructional materials.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may further include one or more of the following components or reagents: one or more reverse transcriptases (RNase H$^+$ and/or RNase H$^-$); an RNase inhibitor (e.g., Superase-In™); an RNase (e.g., RNase H); an enzyme for attaching an oligodeoxynucleotide tail onto the 3' ends of single stranded cDNA molecules (e.g., terminal deoxynucleotidyl transferase); an enzyme for attaching an oligoribonucleotide tail onto the 3' ends of RNA molecules (e.g., poly(A) polymerase); one or more DNA-dependent DNA polymerases (e.g., Klenow enzyme); an enzyme for ligating a double stranded RNA polymerase promoter onto the 3' ends of single stranded DNA molecules (e.g., T4 DNA ligase); one or more RNA-dependent RNA polymerases (e.g., T7 polymerase, T3 polymerase, SP6 polymerase); one or primers comprising a capture nucleotide sequence; one or more second strand DNA synthesis primers; dNTP mix (e.g., dATP, dCTP, dGTP, dTTP); dATP; NTP mix (e.g., ATP, CTP, GTP, UTP); low UTP NTP mix; labeled nucleotides; reaction buffers; salts; nuclease-free water; and/or containers, vials, reaction tubes, and the like compatible with the synthesis of asRNA molecules directly from sRNA molecules according to the methods of the present invention. The components and reagents may be provided in containers with suitable storage media.

Specific embodiments according the present invention will now be described in the following examples. The examples are illustrative only, and are not intended to limit the remainder of the disclosure in any way.

EXAMPLES

Example 1

One Round of sRNA Synthesis Followed by asRNA Synthesis

1. First Strand cDNA Synthesis

For each RNA sample, purified using the RNAqueous® Kit (Ambion), the following RNA/primer mix was prepared on ice:
- 1-8 µl total RNA (not exceeding 2 ng);
- 2 µl first round oligodT sequence specific RT primer (50 ng/µl) (5'-CTC ACT ATA GGG TTT TTT TTT TTT TTT TTT V-3', where V=C, G or A deoxyribonucleotides; SEQ ID NO: 4);
- 1 µl first round random sequence specific RT primer (2× by mass of RNA) (5'-CTC ACT ATA GGG NNN NNN NNN-3, where N=A, G, C or T deoxyribonucleotides at random; SEQ ID NO: 5);
- RNase-free water to 11 µl The first round RT primers have a 5' extension comprising a nucleotide sequence corresponding to the partial 3' end of the non-template strand of the T7 promoter. The RNA/primer mixture was heated at 80° C. for 10 minutes and immediately cooled on ice for 1-2 min. The mixture was then mixed with 9 µl of a Master Mixture solution to bring the final volume to 20 µl containing 1.times. RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. Following a brief centrifugation, the reaction was adjusted to 100 µl with 1.times. TE (10 mM Tris-HCl, pH 8.0, 1 mM EDTA).

2. cDNA Purification

The reaction was purified using the MinElute™ PCR Purification Kit (Qiagen) according to the manufacturer's protocol. Briefly, the cDNA reaction was adjusted to 600 µl with PB buffer provided by the manufacturer. The cDNA reaction was applied to the MinElute™ column and microfuged for 1 minute. The flow-through in the collection tube was discarded, and the column washed with 750 µl PE buffer provided by the manufacturer. The flow-through in the collection tube was discarded, and the column washed with 500 µl 80% ethanol. The flow-through in the collection tube was discarded, and the column microfuged with the cap open for 5 minutes to dry the resin. The column was placed in a clean 1.5 ml microfuge tube, and the column membrane incubated with 10 µl EB buffer provided by the manufacturer for 2 minutes at room temperature. The first strand cDNA molecules were eluted by microfugation for 2 minutes.

3. Tailing of First Strand cDNA

The first strand cDNA molecules were heated at 80° C. for 10 minutes and immediately cooled on ice for 1-2 min. The cDNA molecules in 10 µl were then mixed with 10 µl of a Master Mixture solution to bring the final volume to 20 µl containing 1×tailing buffer (10 mM Tris-HCl, pH 7.0, 10 mM MgCl$_2$), 0.04 mM dATP, and 15 U terminal deoxynucleotidyl transferase (Roche Diagnostics, Indianapolis Ind.). The mixture was briefly centrifuged and incubated at 37° C. for 2 min. The reaction was stopped by heating at 80° C. for 10 min and cooled at room temperature for 1-2 minutes.

4. T7/T3 Promoter Synthesis

One µl of T7/T3 RNA polymerase promoter template oligonucleotide (5'-TAA TAC GAC TCA CTA TAG GGA GAA ATT AAC CCT CAC T-3'; SEQ ID NO: 6) (100 ng/µl) and 1 µl of RNA/DNA composite bridge oligonucleotide (5'-rGrArA rArUrU rArArC rCrCrU rCrArC rUAA AGG GAT TTT TTT TTT TTT T-3'; SEQ ID NO: 7) (100 ng/µl) containing a 3' amino modifier was added to the oligodA-tailed cDNA molecules and the mixture incubated at 37° C. for 10 min to anneal the strands. The T7/T3 RNA polymerase promoter template contains a T7 RNA polymerase promoter template 5' to a T3 RNA polymerase recognition sequence. The tailed cDNA molecules/bridge oligonucleotide/promoter template mixture was then mixed with 3 µl of a Master Mixture solution to bring the final volume to 25 µl containing 1× polymerase buffer (10 mM Tris-HCl, pH 7.0, 10 mM MgCl$_2$, 0.4 mM each dNTP, 200 U Superscript II reverse transcriptase (Invitrogen) and 2 U RNase H (Invitrogen). The mixture was briefly centrifuged and incubated at 37° C. for 30 minutes. The reaction was stopped by heating at 65° C. for 15 min and placed on ice.

5. T7 In Vitro Sense Transcription

One-half of the promoter synthesis reaction (12.5 µl) was heated at 37° C. for 10-15 min to re-anneal the T7T3 promoter strands and then mixed with 12.5 µl of a Master Mixture solution to bring the final volume to 25 µl containing 1× reaction buffer, 7.5 mM each rNTP, and 2 µl T7 RNA polymerase (MEGAscrip™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° C. for 4-16 hrs. It is essential to avoid evaporation and condensation of the reaction during this step.

6. Reverse Transcription of First Round sRNA

Fifty ng of sRNA in a volume of 4 µl was mixed with 2 µl of antisense RT primer (100 ng/µl) (5'-CAT TAA TAC GAC TCA CTA TAG G-3'; SEQ ID NO: 8) and heated at 80° C. for 10 min. The antisense RT primer comprises a nucleotide sequence corresponding to the non-template strand of the T7 promoter and is therefore of sufficient length to anneal to the nucleotide sequence at the 3' ends of the sRNA molecules. The reaction was immediately iced for 2 min, briefly centrifuged, and returned to ice. The mixture was then mixed with 4 µl of a Master Mixture solution to bring the final volume to 10 µl containing 1×RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U MMLV reverse transcriptase (RNase H$^+$) (Promega). The mixture was briefly centrifuged and incubated at 42° C. for 2 hrs. The reaction was stopped by heating at 80° C. for 10 min and cooled at room temperature for 1-2 minutes.

T7 In Vitro Antisense Transcription

The reverse transcription reaction was heated to 37° C. for 10-15 min and then mixed with 14.5 µl of a Master Mixture solution to bring the final volume to 24.5 µl containing 1.times. Reaction buffer, 7.5 mM each rNTP, and 2 µl T7 RNA polymerase (MEGAscript™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° for 4-16 hrs. It is essential to avoid evaporation and condensation of the reaction during this step.

Figure 3:
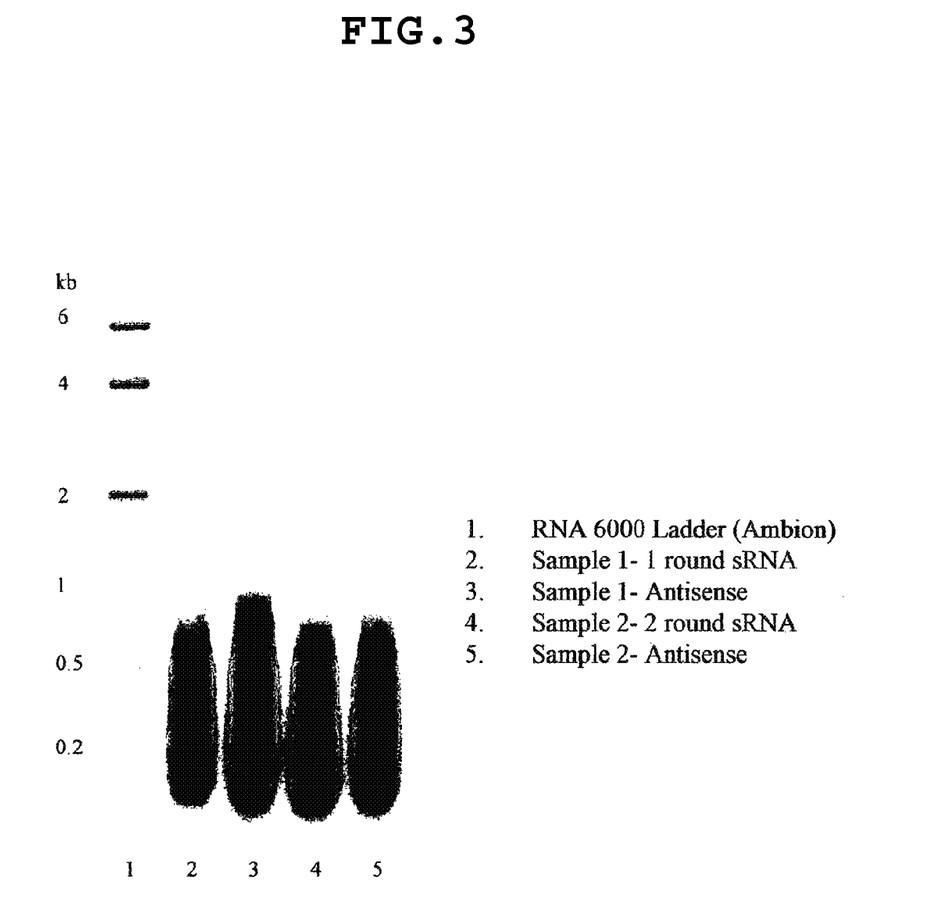
FIG. 3 is a photograph that depicts sRNA and as RNA produced by the methods of the present invention visualized on a 1% agarose gel stained with ethidium bromide.

Replicate amplifications were performed starting with 50 ng of sRNA or water alone (negative control). On average, 25-30 µg of amplified asRNA was recovered after amplifying 50 ng of sRNA vs. 0.5-1 µg of non-specific amplification product when using only water in the reverse transcription reaction. Sense and antisense RNAs were run on a 1% agarose gel to visualize the product size (see FIG. 3, lanes 2 and 3). Generally, the products ranged in size from about 0.1 to 4 kb, which reflects the normal size distribution of mRNA.

Example 2

Two Rounds of sRNA Synthesis Followed by asRNA Synthesis

1. First Strand cDNA Synthesis

For each RNA sample, purified using the RNAqueous® Kit (Ambion), the following RNA/primer mix was prepared on ice:

1-8 µl total RNA (not exceeding 2 ng);
 2 µl first round oligodT sequence specific RT primer (50 ng/pl) (5'-CTC ACT ATA GGG TTT TTT TTT TTT TTT TTT V-3', where V=C, G or A deoxyribonucleotides; SEQ ID NO: 4);
 1 µl first round random sequence specific RT primer (2× by mass of RNA) (5'-CTC ACT ATA GGG NNN NNN NNN-3, where N=A, G, C or T deoxyribonucleotides at random; SEQ ID NO: 5) RNase-free water to 11 µl The first round RT primers have a 5' extension comprising a nucleotide sequence corresponding to the partial 3' end of the non-template strand of the T7 promoter. The RNA/primer mixture was heated at 80° C. for 10 minutes and immediately cooled on ice for 1-2 min. The mixture was then mixed with 9 µl of a Master Mixture solution to bring the final volume to 20 µl containing 1.times. RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. Following a brief centrifugation, the reaction was adjusted to 100 µl with 1.times. TE (10 mM Tris-HCl, pH 8.0, 1 mM EDTA).

2. cDNA Purification

The reaction was purified using the MinElute™ PCR Purification Kit (Qiagen) according to the manufacturer's protocol. Briefly, the cDNA reaction was adjusted to 600 µl with PB buffer provided by the manufacturer. The cDNA reaction was applied to the MinElute™ column and microfuged for 1 minute. The flow-through in the collection tube was discarded, and the column washed with 750 µl PE buffer provided by the manufacturer. The flow-through in the collection tube was discarded, and the column washed with 500 µl 80% ethanol. The flow-through in the collection tube was discarded, and the column microfuged with the cap open for 5 minutes to dry the resin. The column was placed in a clean 1.5 ml microfuge tube, and the column membrane incubated with 10 µl EB buffer provided by the manufacturer for 2 minutes at room temperature. The first strand cDNA molecules were eluted by microfugation for 2 minutes.

3. Tailing of First Strand cDNA

The first strand cDNA molecules were heated at 80° C. for 10 minutes and immediately cooled on ice for 1-2 min. The cDNA molecules in 10 µl were then mixed with 10 µl of a Master Mixture solution to bring the final volume to 20 µl containing 1× tailing buffer (10 mM Tris-HCl, pH 7.0, 10 mM MgCl$_2$), 0.04 mM dATP, and 15 U terminal deoxynucleotidyl transferase (Roche Diagnostics). The mixture was briefly centrifuged and incubated at 37° C. for 2 min. The reaction was stopped by heating at 80° C. for 10 min and cooled at room temperature for 1-2 minutes.

4. T7/T3 Promoter Synthesis

One µl of T7/T3 RNA polymerase promoter template oligonucleotide (5'-TAA TAC GAC TCA CTA TAG GGA GAA ATT AAC CCT CAC T-3'; SEQ ID NO: 6) (100 ng/µl) and 1 µl of RNA/DNA composite bridge oligonucleotide (5'-rGrArA rArUrU rArArC rCrCrU rCrArC rUAA AGG GAT TTT TTT TTT TTT T-3'; SEQ ID NO: 7) mix, briefly centrifuged, and returned to ice. One µl dNTP mix (10 mM each) and 1 µl Superscript™ II reverse transcriptase (200 U/µl; Invitrogen) was added, and the RT reaction incubated at 42° C. for 1 hr. One µl RNase H (2. U/µl) (Invitrogen) was added, and the reaction incubated at 37° C. for 20 min. The reaction was then incubated at 65° C. to stop enzyme activity.

7. T3 Promoter Formation

Two µl of T3 promoter oligonucleotide (50 ng/µl) (5'-GAA ATT AAC CCT CAC TAA AGG G-3'; SEQ ID NO: 10) was added to the second round cDNA reaction. The T3 oligonucleotide is complementary to the T3 RNA polymerase recognition sequence of the initial T7/T3 RNA polymerase promoter template. The reaction was incubated at 37° C. for 10 min to anneal the strands.

8. T3 In Vitro Sense Transcription

The T3 promoter synthesis reaction was mixed with 19 µl of a Master Mixture solution to bring the final volume to 25 µl containing 1× reaction buffer, 7.5 mM each rNTP, and 2 µl T3 RNA polymerase (MEGAscript™ transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° C. for 4-16 hrs. It is essential to avoid evaporation and condensation of the reaction during this step.

9. sRNA Purification and Quantitation

The second round sRNA molecules were purified using the RNeasy Kit (Qiagen) following manufacturer's protocol for RNA cleanup. The purified sRNA molecules were eluted twice in 50 µl RNase-free water and quantified by UV-spectrophotometry in 0.1.times. TE Buffer, pH 8.0 at a wavelength ratio of 260/280.

10. Reverse Transcription of Second Round sRNA

Fifty ng of second round SRNA in a volume of 4 µl was mixed with 2 µl of antisense RT primer (100 ng/µl) (5'-CAT TAA TAC GAC TCA CTA TAG G-3'; SEQ ID NO: 8) and heated at 80° C. for 10 min. The antisense RT primer comprises a nucleotide sequence corresponding to the non-template strand of the T7 promoter and is therefore of sufficient length to anneal to the nucleotide sequence at the 3' ends of the second round sRNA molecules. The reaction was immediately iced for 2 min, briefly centrifuged, and returned to ice. The mixture was then mixed with 4 µl of a Master Mixture solution to bring the final volume to 10 µl containing 1×RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U MMLV reverse transcriptase (RNase H+) (Promega). The mixture was briefly centrifuged and incubated at 42° C. for 2 hrs. The reaction was stopped by heating at 80° C. for 10 min and cooled at room temperature for 1-2 minutes.

11. T7 In Vitro Antisense Transcription

The reverse transcription reaction heated to 37° C. for 10-15 min and then mixed with 14.5 µl of a Master Mixture solution to bring the final volume to 24.5 µl containing 1× reaction buffer, 7.5 mM each rNTP, and 2 µl T7 RNA polymerase (MEGAscript™ transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° C. for 4-16 hrs. It is essential to avoid evaporation and condensation of the reaction during this step.

Replicate amplifications were performed starting with 50 ng of sRNA or water alone (negative control). On average, 25-30 µg of amplified asRNA was recovered after amplifying 50 ng of sRNA vs. 0.5-1 µg of non-specific amplification product when using only water in the reverse transcription reaction. Sense and antisense RNAs were run on a 1% agarose gel to visualize the product size (see FIG. 3, lanes 4 and 5). Generally, the products ranged in size from about 0.1 to 4 kb, which reflects the normal size distribution of mRNA. This size range was maintained even after two rounds of sRNA synthesis.

Example 3

A kit for performing one or more rounds of sRNA synthesis followed by asRNA synthesis was assembled with the following components: First round oligodT reverse transcription primer having a 5' extension comprising a nucleotide sequence corresponding to the partial 3' end of the non-template strand of the T7 promoter (50 ng/µl); First round random reverse transcription primer having a 5' extension comprising a nucleotide sequence corresponding to the partial 3' end of the non-template strand of the T7 promoter (250 ng/µl); 5.times. reverse transcription buffer (250 mM Tris-HCl, pH 8.3, 375 mM KCl, 15 MM MgCl.sub.2, 0.1 M DTT); dNTP mix (10 mM each dATP, dCTP, dGTP, dTTP); Superase-In™ RNase Inhibitor (Ambion); 0.2 mM dATP; 10× tailing buffer (100 mM Tris-HCl, pH 7.0, 100 mM MgCl$_2$); Terminal deoxynucleotidyl transferase (7.5 U/µl); RNA/DNA composite bridge oligonucleotide (100 ng/µl); [0114] T7/T3 RNA polymerase promoter template (50 ng/µl); NTP mix (ATP, GTP, CTP, and UTP) (75 mM each); Low UTP NTP mix (75 mM ATP, 75 mM GTP, 75 mM CTP, and 25 mM UTP); 10×RNA polymerase reaction buffer (Ambion); Second round reverse transcription primer comprising a nucleotide sequence corresponding to the specific nucleotide sequence of the 5' extension of the first round reverse transcription primers (50 ng/µl); T7 promoter oligonucleotide (50 ng/µl); T3 promoter oligonucleotide (50 ng/µl); T7 enzyme mix (Ambion); T3 enzyme mix (Ambion); RNase H (2 U/µl); Antisense reverse transcription primer comprising a nucleotide sequence corresponding to the non-template strand of the T7 promoter (50 ng/µl); MMLV reverse transcriptase RNase H$^+$ (Invitrogen); and Nuclease-free water.

The components were placed in numbered vials and placed in a container with a printed instruction manual for multiple rounds of sRNA synthesis using the kit components.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A kit for synthesizing asRNA molecules and/or cDNA molecules from a sRNA, the kit comprising:

a) a first primer complementary to a 3' end of a first sRNA, the first primer having a 5' extension comprising a nucleotide sequence corresponding to a partial 3' end of the non-template strand of a consensus RNA polymerase recognition sequence and extending less than 19 nucleotides, for synthesizing a second sRNA from the first sRNA which has a 3' end comprising a partial 5' end of a template strand of the consensus RNA polymerase recognition sequence less than 19 nucleotides in length;

b) a second primer comprising a nucleotide sequence corresponding to a most 5' end of a non-template strand of the consensus RNA polymerase recognition sequence, wherein the second primer is of sufficient length to anneal to the consensus RNA polymerase recognition sequence at the 3' end of the second sRNA and provide a complete non-template strand of the consensus RNA polymerase recognition sequence upon reverse transcription of the second sRNA using the second primer; and c) instructional materials for synthesizing asRNA and/or cDNA molecules from the first sRNA using the first primer and the one or more second primers.

2. The kit of claim 1, further comprising one or more reagents and instructional materials for synthesizing the second sRNA.

3. The kit of claim a 2, wherein the one or more reagents comprise a single stranded promoter template comprising at least one RNA polymerase recognition sequence; and a single stranded RNA/DNA composite bridge oligonucleotide comprising a RNA sequence 5' of a DNA sequence.

4. The kit of claim 3, further comprising one or more third primers comprising a nucleotide sequence corresponding to the nucleotide sequence of the 5' extension of the first primer; and a single stranded promoter oligonucleotide complementary to a second RNA polymerase recognition sequence of the promoter template.

5. The kit of claim 1, wherein the 5' extension of the first primer ranges from about 8 to about 12 nucleotides.

\* \* \* \* \*

UNITED STATES PATENT AND TRADEMARK OFFICE
CERTIFICATE OF CORRECTION

PATENT NO. : 8,653,251 B2  
APPLICATION NO. : 13/013000  
DATED : February 18, 2014  
INVENTOR(S) : Robert C. Getts, James Kadushin and Kelly Sensinger Page 1 of 1

It is certified that error appears in the above-identified patent and that said Letters Patent is hereby corrected as shown below:

On the Title Page
Item (73) Assignee: "Genisphere Inc., Hatfield, PA (US)" should be changed to --Genisphere, LLC, Hatfield, PA (US)--.

Signed and Sealed this
Fifth Day of August, 2014

Michelle K. Lee
*Deputy Director of the United States Patent and Trademark Office*